United States Patent [19]

Fuller

[11] Patent Number: 5,314,595
[45] Date of Patent: May 24, 1994

[54] ELECTROPHORESIS OF NUCLEIC ACID FRAGMENTS

[75] Inventor: Carl M. Fuller, Cleveland Heights, Ohio

[73] Assignee: United States Biochemical Corporation, Cleveland, Ohio

[21] Appl. No.: 862,734

[22] Filed: Apr. 3, 1992

[51] Int. Cl.$^5$ .................. G01N 27/26; G01N 27/447
[52] U.S. Cl. .................. 204/182.8; 204/299 R
[58] Field of Search .................. 204/299 R, 182.8

[56] References Cited

U.S. PATENT DOCUMENTS

| | | | |
|---|---|---|---|
| 4,416,761 | 11/1983 | Brown et al. | 204/182.8 X |
| 4,726,889 | 2/1988 | Love et al. | 204/182.8 |
| 4,795,699 | 1/1989 | Tabor et al. | 435/5 |
| 4,844,786 | 7/1989 | Sugihara et al. | 204/299 R |
| 4,936,963 | 6/1990 | Mandecki et al. | 204/182.8 |
| 5,041,371 | 8/1991 | Cowan et al. | 435/91 X |
| 5,075,216 | 12/1991 | Innis et al. | 435/6 |

FOREIGN PATENT DOCUMENTS 9204625 3/1992 PCT Int'l Appl. .

OTHER PUBLICATIONS

Carninci et al., 18 *Nucleic Acids Research* 204, 1989.
Richards et al., 12 *Analytical Biochemistry* 452, 1965.
Peacock and Dingman, 6 *Biochemistry* 1818, 1967.
Ansorge and Barker, 9 *J. Bioc. Biop. Meth.* 33, 1984.
Brumley and Smith, 19 *Nucleic Acids Research* 4121, 1991.
Wyckoff et al., 78 *Analytical Biochemistry* 459, 1977.
Fuller, United States Biochemical Corp. brochure.

Primary Examiner—John Niebling
Assistant Examiner—John S. Starsiak, Jr.
Attorney, Agent, or Firm—Lyon & Lyon

[57] ABSTRACT

A method for electrophoresis of nucleic acid fragments present in the solution which contains an amount, e.g., 0.2% or more, of a reagent, e.g., glycerol, dithiothreitol (DTT) and trehalose or other sugars, which interact to form a complex with borate or boric acid. The method includes applying the solution to an electrophoretic gel and electrophoresing those fragments into the gel in the presence of a buffer lacking boric acid, or a derivative thereof, which forms a chelate complex with the reagent and thereby causes distortion of electrophoresis of the fragments in a gel including such a buffer.

3 Claims, 3 Drawing Sheets

FIG. 1a.
A
+ Glycerol
G A T C
FIG. 1b.
B
No Glycerol
G A T C
FIG. 2a.
A
+ Glycerol
G A T C
FIG. 2b.
B
No Glycerol
G A T C
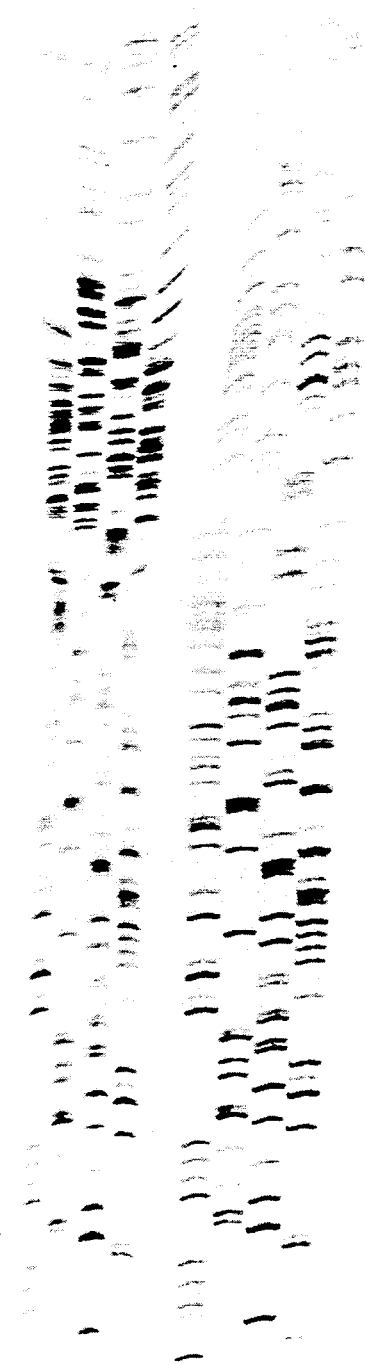
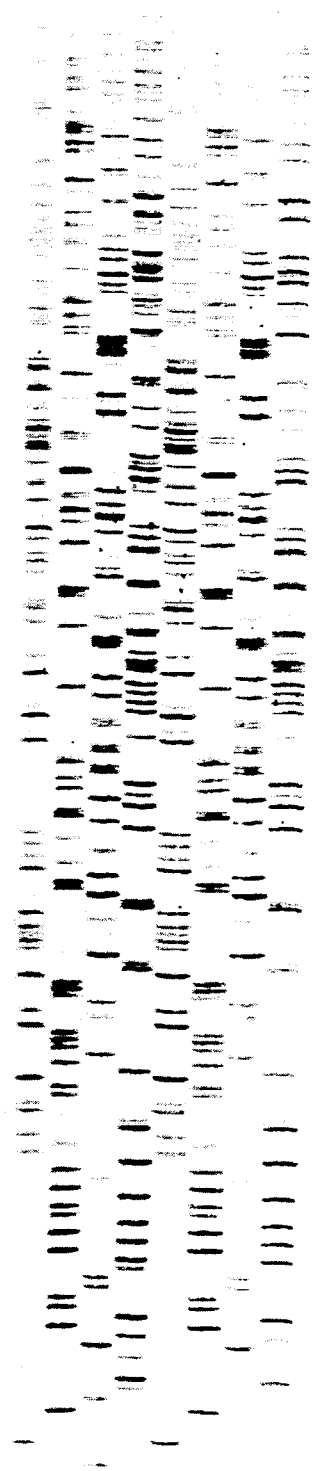

A
No Glycerol
10 min   20 min   40 min
G A T C  G A T C  G A T C

B
6.25% Glycerol
10 min   20 min   40 min
G A T C  G A T C  G A T C

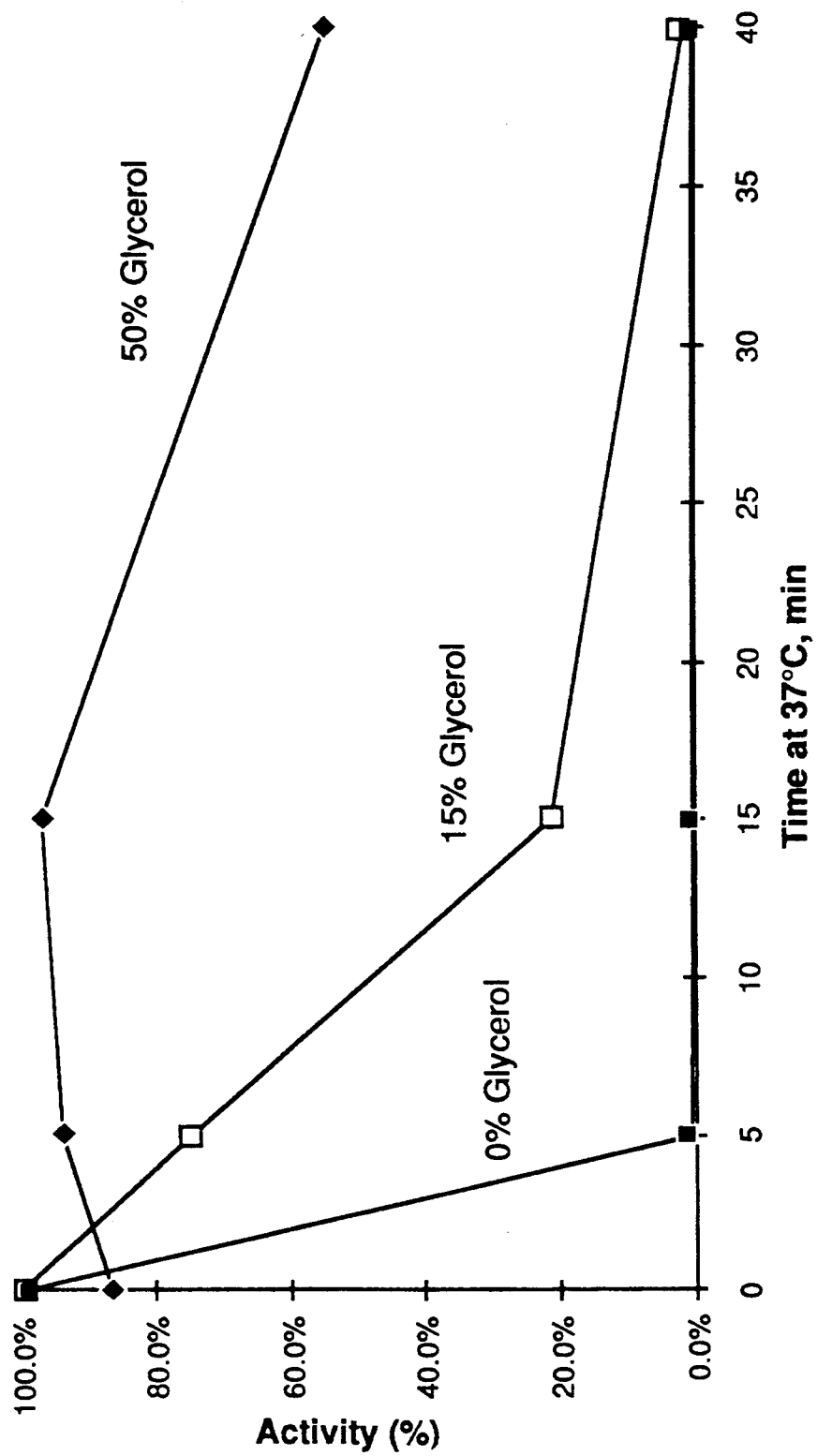

ELECTROPHORESIS OF NUCLEIC ACID FRAGMENTS

FIELD OF THE INVENTION

This invention relates to methods and kits for electrophoresis of nucleic acid fragments, particularly those methods and kits useful for electrophoresing nucleic acid fragments contained in a solution which includes glycerol.

BACKGROUND OF THE INVENTION

Fuller, 16 *Comments* 1989 reports that the presence of glycerol in a sample loaded on an electrophoretic gel may cause artifacts, such as distortion of nucleic acid fragments in DNA sequencing gels. The distortion is said to resemble a bulge in the sequencing gel, and renders the 400–600 nucleotide region of the gel unreadable. Fuller states that because of the distortion caused by the presence of glycerol, United States Biochemical Corporation supplies a sequencing enzyme, SEQUENASE Version 2.0 T7 DNA polymerase, at a high enough concentration so that no glycerol distortion occurs when the enzyme is diluted prior to use.

Carninci et al. 18 *Nucleic Acids Research* 204, 1989 describe a standard sequencing gel system using Tris/Borate/EDTA buffer (TBE). It also describes a discontinuous buffer system using Tris-sulphate and Tris-borate. The Tris-sulphate is used as a running gel buffer, and Tris-borate as a tank buffer.

Richards, et al., 12 *Analytical Biochemistry* 452, 1965 and Peacock and Dingman, 6 *Biochemistry* 1818, 1967 describe electrophoresis of ribonucleic acid in polyacrylamide gels and resolution of multiple RNA species by polyacrylamide gel electrophoresis. Richards, et al., describe use of Tris-HCl buffer as well as acetic, cacodylic, diethyl barbituric, and glycyl glycine buffers. Peacock and Dingman describe use of Tris-EDTA and boric acid buffers for electrophoresis. The RNA species are not provided in glycerol-containing samples.

Ansorge and Barker, 9 *J. Bioc. Biop. Meth.* 33, 1984 describe use of Tris/Tricine buffer and an ammediol system for electrophoresis of Maxam and Gilbert DNA sequencing products. Such products are provided in samples without glycerol.

Brumley and Smith, 19 *Nuc. Acid. Res.* 4121, 1991 describe use of a borate buffer for a sequencing gel.

SUMMARY OF THE INVENTION

The present invention concerns use of an electrophoretic buffer, for electrophoresis of nucleic acids, which does not form a chelate complex with glycerol or other reagents. Such complexes, e.g., between boric acid and glycerol, are described by Cotton and Wilkinson, *Advanced Inorganic Chemistry*, 1980, John Wiley & Sons, p. 298. Other such complexes may be formed between borate and various sugars, such as ethylene glycol, trehalose or dithiothreitol (DTT) which may be used as stabilizing agents for an enzyme (e.g., trehalose is used by Quadrant for stabilizing a dried enzyme preparation). The presence of such a complex within an electrophoretic gel causes distortion of negatively charged DNA molecules within the gel. The complex is negatively charged under electrophoretic gel conditions and migrates through the gel along with the negatively charged DNA. It is present in sufficient amount to overload the gel, causing distortion of adjacent DNA bands within the gel.

Applicant has discovered that substitution of a different weak acid for boric acid in an electrophoretic gel buffer eliminates gel distortion. The invention features a method for electrophoresis of nucleic acid fragments, such as those produced during DNA sequencing procedures, by use of a buffer which does not form a complex with glycerol or other reagents. This enables use of glycerol or the other reagents at high concentrations in DNA sequencing reactions or other reactions concerning nucleic acids. Such high concentrations are advantageous because they are more convenient and they increase the stability of the enzymes within a reaction mixture.

Thus, in the first aspect the invention features a method for electrophoresis of nucleic acid fragments present in the solution which contains an amount, e.g., 0.2% or more, of a reagent, e.g., glycerol, DTT, and trehalose or other sugars, which interacts to form a complex with borate or boric acid. Generally, boric acid may react with any 1,2-diol compound, and the stability of the product depends on the relative orientation of the alcohols. Thus, complexes with trans glycols are weaker than with cis glycols. Examples of such 1,2-diols (glycols) include ethylene glycol, propylene glycol, butylene glycol, threitol, erythrotol, dithioerythrotol, pinacol, ribose, mannitol, glucitol, ribitol, sorbitol, inositols, Span® and Tween® detergents, sorbose, ascorbic acid, Ficoll®, dextran, and derivatives thereof. Various sugars will also react, including glyceraldehyde, erythrose, threose, arabinose, xylose, lyxose, allose, altrose, glucose, mannose, gulose, idose, galactose, talose, fructose, ribulose, xylulose, fucose, rhamnose, fructose, glycosides of these, sucrose and other oligosaccharides, polysaccharides, cellobiose, maltose, lactose, trehalose, gentobiose, melibiose, cellulose, and starches. Amino-sugars, acylaminosugars and glycosides may also react. That is, any compound having a 1,2-diol moiety which reacts with borate to form an anionic chelate complex is best avoided in gel compositions and reagents run into a gel. The method includes applying the solution to an electrophoretic gel and electrophoresing those fragments into the gel in the presence of a buffer lacking boric acid, or a derivative thereof, which forms a chelate complex with the reagent and thereby causes distortion (i.e., makes reading of the DNA sequence more difficult than if there were no distortion) of electrophoresis of the fragments.

In preferred embodiments, the fragments are produced during an enzymatic DNA sequencing reaction; the gel is a DNA sequencing gel; the reaction is performed in the presence of the glycerol; and the acid portion of the buffer is selected from acetic acid, carbonic acid, glycine, serine, taurine, tricine, and bicine. The basic portion may be Tris or ammediol or any other equivalent buffer components.

In a related aspect, the invention features a kit for DNA sequencing which includes reagents, e.g., DNA polymerase, necessary for DNA sequencing, and an electrophoretic buffer selected from those described above. Most preferably, the polymerase is provided at a concentration in a glycerol-containing buffer which does not need dilution prior to use (e.g., within a microtitre well format). By not needing dilution is meant that the DNA polymerase can be used directly in a sequencing reaction without a step of dilution of the enzyme prior to addition to other components and in a volume that can be readily and accurately transferred by commonly available pipetting devices (2 μl of 50% glycerol solution).

Prior to this invention, SEQUENASE DNA polymerase and Taq DNA polymerase were provided at high concentration (e.g., at 13 U/μl for SEQUENASE DNA polymerase and 32 U/μl for Taq DNA polymerase) in a sequencing kit (in 50% glycerol) and the customer was forced to dilute it 8-fold (e.g., to 1.6 U/μl or 4 U/μl for SEQUENASE DNA polymerase and Taq DNA polymerase, respectively) prior to use. This represents a compromise among convenience, stability and gel readability. When diluted in the labeling reaction mixture (without glycerol), SEQUENASE DNA polymerase remains stable only 10-15 minutes at room temperature in the first step of the sequencing reaction, but the reaction can be completed in 5 minutes and the gel distortion is acceptably small. The polymerase, however, is stable if diluted in the presence of glycerol.

The present invention eliminates the distortions on the gels, by using a new gel buffer in place of the traditional TBE buffer. The use of this new buffer provides the following advantages:

1. The SEQUENASE or Taq DNA polymerase can be supplied pre-diluted in 50% glycerol, eliminating a tedious step in the sequencing protocol. It can simply be added directly from the kit vial in a convenient volume of 2 μl.

2. Enzyme dilution buffer is not required in a sequencing kit.

3. The enzyme can be much more stable in use, allowing more leeway (in time and temperature) in the manner the reactions are run. This allows easier dispensing of enzyme by slow automated equipment during use. There are distinct improvements in sequencing results with higher concentrations of glycerol, especially with double-stranded templates.

4. Contaminants in the template which may destabilize the enzyme are less troublesome.

5. The end user of a typical 100 test DNA sequencing kit will prefer receiving a vial containing 200 μl of enzyme over the current 25 μl. This way, it is possible to run just one reaction without wasting enzyme in dilution.

6. Elimination of the gel distortion caused by glycerol is particularly useful for procedures which make use of added restriction enzymes and gene 6 exonuclease, such as lambda DNA sequencing.

7. A microtiter-plate format sequencing kit can be more readily produced. The reagents (including enzyme) can be pre-dispensed in 96-well plates and used to sequence 1-12 templates simultaneously. Unused portions of the plate can be returned to the freezer for later use.

8. When sufficient glycerol is added to reactions run with SEQUENASE T7 DNA Polymerase, the termination reactions can be run at high temperature by pre-warming the termination reaction vials to 70° C. This high temperature may eliminate template secondary structure problems.

Other features and advantages of the invention will be apparent from the following description of the preferred embodiments thereof, and from the claims.

DESCRIPTION OF THE PREFERRED EMBODIMENTS

The drawings will first briefly be described.

Drawings

FIG. 1 is a reproduction of an autoradiogram of a DNA sequencing gel formed in the presence of a borate buffer showing that glycerol causes gel distortions;

FIG. 2 is a reproduction of an autoradiogram of a DNA sequencing gel formed in the absence of a borate buffer showing that glycerol causes no distortion on a gel made using a glycerol-tolerant buffer;

Figure 3A:

FIGS. 3A & B are reproductions of autoradiograms of a DNA sequencing gel in which DNA sequencing reactions are run in the absence or presence of glycerol; and FIG. 4 is a graphical representation showing that glycerol stabilizes the activity of a T7 DNA polymerase.

GEL ELECTROPHORESIS

Current methods for sequencing DNA rely on electrophoresis gels to resolve DNA fragments according to their size or molecular weight, Maxam and Gilbert, 65 *Methods in Enzymology* 499, 1980, Maxam and Gilbert, 74 *Proc. Nat. Acad. Sci. USA* 560, 1977, Sanger, et al., 74 *Proc. Nat. Acad. Sci. USA* 5463, 1977. A population of DNA fragments is prepared in such a way that all the fragments have a particular sequence at one end, and at the other end have generally only one (of the four possible) nucleotides. Thus, the presence of a fragment containing 50 nucleotides (in addition to a region known as a primer) in the population of adenosine-terminated fragments indicates that adenosine is present in the 50th position of the sequence.

High-resolution separation of DNA fragments by size is an essential component of a sequencing method. Sequencing gels are typically larger and thinner than other kinds of electrophoresis gel, so that high possible resolution is achieved, resulting in the determination of large numbers of bases in a single electrophoresis run. Gels typically resolve 150-300 nucleotides in a single run, but there have been reports of resolving 500 or more bases using particularly long gels, or special apparatus. Tabor & Richardson, 84 *Proc. Natl. Acad. Sci. USA* 4767, 1987, Sieminiak et al., 192 *Anal. Biochem.* 441, 1991.

Examples of sequencing gels now in use generally include 6-8% polyacrylamide crosslinked with N, N'-methylene bisacrylamide (20:1 acrylamide to bisacrylamide to bisacrylamide by weight), 7-8.3M urea and TBE buffer (10.8 g tris (hydroxymethyl) aminomethane ("Tris"), 0.93 g disodium EDTA, and 5.5 g boric acid per liter of solution) to give final concentrations of 0.09M Tris, 0.09M boric acid and 0.0025M EDTA. This buffer was first described by Peacock and Dingman in 6 *Biochemistry* 1818, 1967 for the separation of RNA species by polyacrylamide gel electrophoresis. The addition of urea to this buffer to denature the DNA was described by Maniatis, et al. in 14 *Biochemistry* 3787, 1975, and for sequencing DNA by Air, et al. in 108 *J. Mol. Biol.* 519, 1976.

The composition of sequencing gels has not changed significantly since 1976, although some workers use formamide, alternative crosslinkers, and reagents which bind the gel to glass.

The DNA Polymerase used for performing a sequencing reaction to form the desired DNA fragment preparations is stored in 50% glycerol to keep it stable at reaction temperatures or during storage at −20° C. It is difficult to accurately transfer volumes of less than 2

μl of 50% glycerol. Thus, it is necessary to dilute the DNA polymerase immediately prior to use, thereby diluting the glycerol to acceptable levels. Alternatively, the samples are purified by precipitation with ethanol prior to loading on the gel.

While these measures eliminate the gel-distortion problem, they are somewhat cumbersome, and time consuming. Thus, the present invention features a new gel formulation which tolerates glycerol in the sample. Since the polymerase can be maintained in high concentrations of glycerol at all times, potential problems which result from enzyme inactivation are eliminated.

When glycerol is applied to an ordinary TBE-buffered DNA sequencing gel, it complexes with boric acid and migrates through the gel. If the quantity of glycerol is large enough to overload the gel, it distorts the region of the gel in which it migrates. The degree of distortion depends on the amount of glycerol loaded and the size of the gel. When following the nominal protocol used for the SEQUENASE DNA sequencing kits, 10.7 μg of glycerol is loaded into each sequencing gel lane along with about 0.25 μg of DNA. This amount of glycerol does not normally interfere with DNA migration on the gel. If the enzyme is diluted in a buffer containing 50% glycerol, more than 85 μg of glycerol is present in the sample applied to the lane. This quantity is enough to severely distort the pattern of DNA band migration. Typical amounts of glycerol loaded on a sequencing gel are listed in Table 1.

TABLE 1

| Glycerol Concentration (%) | Sequenase Kits | Taquence Kits | Sequenase Kit, no Enzyme Dilution | 96-well Kit as described |
|---|---|---|---|---|
| Enzyme | 50 | 50 | 50 | 50 |
| Diluted Enzyme | 6.25 | 6.25 | 50 | 50 |
| Labeling Reaction | 0.806 | 0.714 | 6.45 | 25.9 |
| Termination Reactions | 0.470 | 0.357 | 3.76 | 15.9 |
| Final Sample | 0.282 | 0.238 | 2.26 | 9.85 |
| Amount of Glycerol Loaded on Typical Electrophoresis Gel Lane (3 μl) | | | | |
| μl Glycerol per lane | 0.008 | 0.007 | 0.068 | 0.295 |
| μg Glycerol per lane | 10.7 | 9.00 | 85.3 | 372 |

Appropriate gel buffers can be determined by routine experimentation to find those which are useful in DNA separations and yet do not complex with glycerol or various sugars to form a distorting complex. For example, for the acid component weak acids can be used, including the following acids, which serve to replace boric acid in DNA sequencing gels: acetic acid, carbonic acid, glycine, serine, taurine, tricine (N-tris (hydroxyethyl) methylglycine), and bicine (N, N-bis(2-hydroxyethyl)glycine). Of these, the stronger acids (acetic and carbonic) yield buffers with higher conductivity than desired for routine use. The weakest acid, glycine, yields a buffer with a pH somewhat higher than normally used, although results are acceptable. The others all yield buffers with electrophoretic properties essentially identical to those of borate-containing buffers, but the addition of high concentrations of glycerol has no effect on the gel resolution. Glycine and taurine are preferred at present since they are less expensive than some of the other acids, and more soluble than D,L-serine. Other organic and inorganic acids could also be used, particularly those with a pKa value between 7 and 10 at 40°-50° C. For example, TAPS (3-[N-tris-(hydroxymethyl) methyl-amino]-propanesulfonic acid), CHES (2-(N-cyclohexylamino) ethanesulfonic acid), AMPSO (3-[dimethyl (hydroxymethyl)-methylamino]-2-hydroxypropanesulfonic acid), CAPSO (3-(cyclohexylamino)-2-hydroxy-1-propanesulfonic acid), CAPS (3-N-(Cyclohexylamino)-propanesulfonic acid), Glycylglycine, Threonine, allo-Threonine, arginine, 2-aminoethyl sulfuric acid, and glutamic acid.

EXAMPLES

The following buffers have been prepared and tested for running DNA sequencing gels. Typically, they were used as follows:

1. Buffer was prepared in concentrated form (usually 10-fold concentrate) with the quantities of reagents shown in Table 2.

2. A sequencing gel was prepared by mixing 7.6 g acrylamide, 0.4 g N, N'-methylene bisacrylamide, 42 g urea, concentrated buffer and water to a final dissolved volume of 100 ml. The volume of concentrated buffer was usually 10 ml but varied in actual experiments. Actual volumes used are listed in Table 2. The mixture was dissolved by gentle stirring at room temperature (about 20° C.).

3. The mixture was filtered either through Whatman #1 filter paper or a 0.4 μm nitrocellulose filter. Gel molding plates, spacers and comb were assembled using tape and clamps by standard procedures. The gel apparatus used is a model STS 45 from IBI division of Kodak. Gels were approximately 42 cm high, 37 cm wide and 0.4 mm thick, run with a 64-well "sharkstooth" comb.

4. When ready, 1.0 ml of 10% ammonium persulfate and 25 μl of N,N,N',N'-tetramethylethylenediamine were added to the gel forming solution and the gel poured immediately. Gels were typically used within 2-3 hours of pouring but sometimes used after sitting overnight at room temperature.

5. Gels were loaded with sequencing reaction products, labeled with $^{35}S$ prepared using the USB SEQUENASE ® Version 2.0 DNA sequencing kit and M13mp18 DNA for template.

6. Running buffer (1000 ml) was prepared by diluting the same concentrated buffer by the same ratio as for preparing the gel. Thus, the same buffer was present in the upper and lower chambers and in the gel itself. Gels were run at constant power (60-70 watts) until the bromophenol blue dye reached the bottom, typically 2-3 hours. The voltage and current required to maintain 60-70 watts varied in accordance with the conductivity of the buffer. Gels prepared with buffers of high conductivity generally ran slower. 7. Gels and sequencing reactions were also prepared for running on the Applied Biosystems Model 373A automated DNA sequencing instrument according to the instructions of the instrument manufacturer except for the substitution of buffer. These gels also were free of glycerol-induced artifacts and gave normal sequencing results. 8. These buffers also work for running horizontal agarose gels for the separation of DNAs much like the currently popular TBE and TAE buffers.

TABLE 2

| Buffer | Weak acid used (pKa at 45° C.) | Composition; g/ 500 ml Buffer Concentrate | | | pH (1:10) | Conductivity (of a 1:10 dilution) μmho/cm | Dilution for Gel ml/100 ml of Gel |
| --- | --- | --- | --- | --- | --- | --- | --- |
| | | Weak Acid | Tris | Na₂ EDTA | | | |
| 1 (TBE) | Boric Acid (9.1) | 28 | 54 | 4.5 | 8.16 | 755 | 10 |
| 2 | Bicine (7.9) | 50 | 54 | 4.5 | 8.20 | 1000 | 6.67 |
| 3 | D,L-Serine (8.7) | 35 | 54 | 4.5 | 8.47 | 734 | 10 |
| 4 | Acetic Acid (4.8) | a | 54 | 4.5 | 8.10 | 1150 | 10 |
| 5 | Carbonic Acid (6.3) | b | 54 | 4.5 | 8.23 | 1070 | 10 |
| 6 | Glycine (9.3) | 50 | 54 | 4.5 | 8.53 | 700 | 10 |
| 7 | Glycine (9.3) | 33.75 | 20 | 4.5 | 8.45 | 435 | 15 |
| 8 | Glycine (9.3) | 80 | 108 | 9 | 8.6 | 1500 | 5 |
| 9 | Tricine (7.6) | 15 | 54 | 4.5 | 8.23 | 1075 | 6.67 |
| 10 | Taurine (8.6) | 10 | 54 | 4.5 | 8.85 | 560 | 10 |
| 11 | Taurine (8.6) | 18 | 54 | 4.5 | 8.65 | 750 | 10 |
| 12 | Taurine (8.6) | 20 | 54 | 4.5 | 8.70 | 800 | 10 |
| 13 | Taurine (8.6) | 25 | 54 | 4.5 | 8.60 | 890 | 10 |
| 14 | Taurine (8.6) | 35 | 54 | 4.5 | 8.45 | 950 | 10 |

<sup>a</sup>Acetic acid was added until the pH of the concentrated buffer was 8.3. This required approximately 12 ml of acetic acid.
<sup>b</sup>The solution of Tris and EDTA was bubbled with $CO_2$ until the pH of the concentrated buffer was 8.3.

EXAMPLE 1

Referring to FIG. 1, the gel picture demonstrates that glycerol causes sequencing gel distortions. One set of four DNA sequencing reactions was run using the SEQUENASE® Version 2.0 DNA sequencing kit (USB) using M13mp18 template DNA and $\alpha$-$^{35}$S dATP following the methods supplied with the kit. The final reaction products (G, A, T and C reactions, 10 μl each) were divided into two equal portions and 1 μl of 50% glycerol was added to one portion, resulting in a total glycerol concentration of about 8.6%. A 3μl portion of these were loaded onto an 8% polyacrylamide sequencing gel prepared with normal TBE buffer. The four left-hand lanes contained the added glycerol such that 0.26 μl or 324 μg of glycerol was loaded into each lane. The distortion in these lanes is so severe that it also distorted the four adjacent lanes which carried the samples without added glycerol (total glycerol concentration about 0.28% so that total of 0.0085 μl or 10.7 μg glycerol was loaded onto each lane). Other experiments have shown that while samples containing this amount of glycerol are essentially free of distortion, ones with twice this amount and above exhibit distortions which can interfere with readability of the gel.

EXAMPLE 2

Referring to FIG. 2, the gel picture demonstrates that glycerol causes no distortion on a gel made using a glycerol-tolerant buffer. Samples were prepared identically with those discussed above in Example 2, and were run on an 8% polyacrylamide gel using a buffer which contained taurine in place of boric acid. This buffer has the composition and properties of buffer 11 in Table 2. There is no evidence of any distortion even with this very high concentration of glycerol.

EXAMPLE 3

Figure 3B:
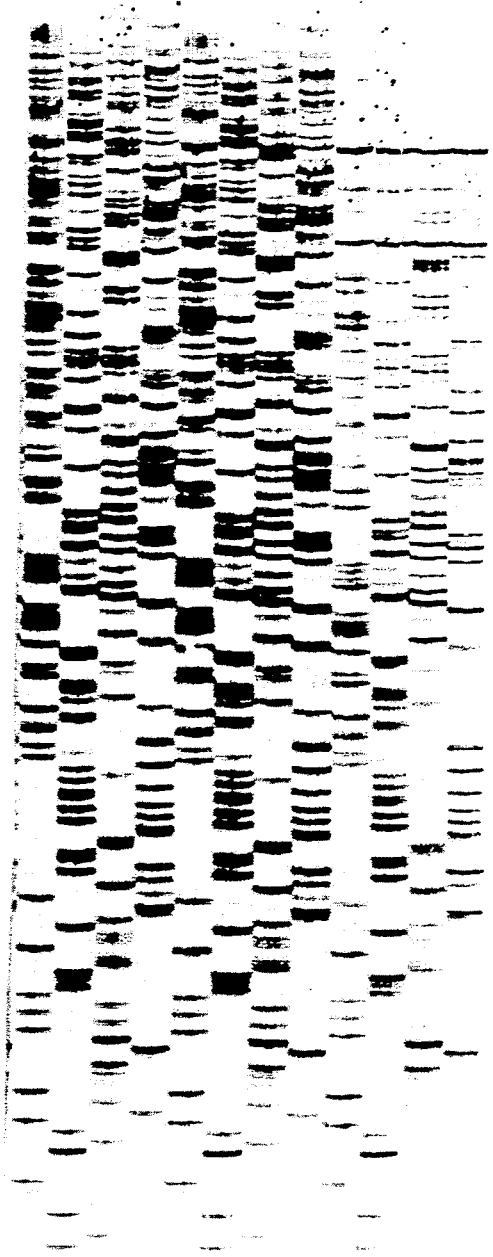

Referring to FIGS. 3A and 3B, the gel pictures demonstrate that DNA sequencing results can be improved if the reactions are run with added glycerol. Sequencing reactions were run as described in Example 1 except that the labeling step was run at 41° C. for 10, 20 or 40 min. as indicated. In FIG. 3A, the enzyme was diluted normally so that the concentration of glycerol present during the labelling step was 0.8%. In FIG. 3B the enzyme was diluted using dilution buffer that contained 50% glycerol so that the concentration of glycerol present during the labelling step was 6.5%. The gel was identical to the one described in FIG. 2. Under these conditions, sequencing reactions run poorly with low glycerol concentration but the performance was restored when sufficient glycerol was added. If these sequences had been run on a normal TBE gel, severe distortions would have been evident.

EXAMPLE 4

Referring to FIG. 4, the graph demonstrates that glycerol stabilizes the activity of a modified T7 DNA polymerase. Samples of SEQUENASE Version 2.0 T7 DNA polymerase at a concentration of 0.5 Units/μl were incubated at 37° C. for the times indicated in 10 mM Tris-HCl (pH 7.5), 5 mM DTT and 0.5 mg/ml bovine serum albumin containing either no added glycerol, 15% glycerol or 50% glycerol as indicated. After incubation at 37° C., the samples were chilled on ice and assayed by a standard procedure. Assay reaction mixtures (100 μl) contained 40 mM Tris-HCl pH 7.5, 10 mM $MgCl_2$, 5 mM DTT, 0.3 mM dGTP, dCTP, dATP and [$^3$H]dTTP, 5 μg of M13mp18 single-stranded DNA pre-annealed to 5 pmol universal (−20) primer and enzyme. The enzyme (10 μl ) was added last to the pre-warmed (37° C.) reaction mixture and incubation was for 1 min. at 37° C. The reaction was stopped by the addition of 20μl of 5 mg/ml fish-sperm DNA and 3 ml of 1N HCl, 0.1M sodium pyrophosphate and acid-insoluble radioactivity determined by filtration using glass-fiber filters. Enzyme incubated in the absence of glycerol was inactivated within 5 min. under these conditions but remained at least 50% active even after 40 min. in the presence of 50% glycerol.

EXAMPLE 5

Buffers without EDTA

Buffers without EDTA present in them are particularly useful in this invention, e.g., buffers containing 40 g glycine, 54 g Tris in 500 ml, pH 8.6 and having a conductivity of 500 μmho/cm, can be used at a 1:10 dilution. Without EDTA bands at the bottom of gels are improved in separation and clarity.

Kits

SEQUENASE and TAQuence kits presently require dilution of enzyme 8-fold prior to use. The present invention allows production of a kit in which the reagents are re-formulated to contain enzyme at ⅛th the normal concentration in a 50%-glycerol solution so that the kit enzyme can be used directly without dilution. Such a kit will save the user time, and possibly allow the user more actual sequences per kit and more flexible use of the enzyme in situations where only 1 or 2 sequences are being performed on a given day. Since the sequencing reaction products will contain large quantities of glycerol, a glycerol-tolerant gel formulation of this invention, or the extra work of removing glycerol from the products will be required.

A new kit can also be produced, perhaps in a 96-well plate format, which consists of pre-dispensed reagents for sequencing. The enzyme can be dispensed at its final working concentration in 50% glycerol buffer, in which it is stable even for a 15-20 minute incubation at 37° C. Other reaction components whose volumes are critical can also be dispensed using 30-50% glycerol which prevents the component from freezing under the plate storage condition ($-20°$ C.) and prevents loss by evaporation (or lyophylization) which occurs when covered plates are frozen. Components whose volume are not critical can simply be dispensed in the plate in convenient amounts. A possible configuration is as follows:

|              | 1 | 2 | 3 | 4 | 5 | 6 | 7 | 8 | 9 | 10 | 11 | 12 |
|--------------|---|---|---|---|---|---|---|---|---|----|----|----|
| Enzyme       | O | O | O | O | O | O | O | O | O | O  | O  | O  |
| Labeling Mix | O | O | O | O | O | O | O | O | O | O  | O  | O  |
| Stop Solution| O | O | O | O | O | O | O | O | O | O  | O  | O  |
| Buffer       | O | O | O | O | O | O | O | O | O | O  | O  | O  |
| ddGTP Mix    | O | O | O | O | O | O | O | O | O | O  | O  | O  |
| ddATP Mix    | O | O | O | O | O | O | O | O | O | O  | O  | O  |
| ddTTP Mix    | O | O | O | O | O | O | O | O | O | O  | O  | O  |
| ddCTP Mix    | O | O | O | O | O | O | O | O | O | O  | O  | O  |

The template DNA and primer are added to the buffer well and the entire plate incubated at 37° C. for 10 minutes to anneal. Then the labelled nucleotide, labeling mix and enzyme are added to the buffer well and the labeling step incubated for about 5 min. at room temperature. The temperature of the plate is increased to 37° C. and one quarter of the mixture then transferred to each of the ddNTP mixes in the lower wells for the termination step (at least 5 min.). Finally, stop solution is transferred from its well to the termination reactions. Since the timing of the steps is not critical, up to 12 templates can be sequenced at once. When fewer templates are to be sequenced, an appropriate area of the plate can simply be cut with scissors and used.

For automated pipetting devices, it is critical that the final total volume of the labeling reaction be known, so evaporation or condensation of the buffer, enzyme and labeling mix during cold storage must be minimized. This can be accomplished by the addition of 30-50% glycerol or ethylene glycol which prevents freezing and evaporation or lyophylization. Since the sequencing reaction products will contain large quantities of glycerol, a glycerol-tolerant gel formulation or the extra work of removing glycerol from the products will be required.

Other embodiments are within the following claims.

I claim:

1. A method for electrophoresis, through a gel comprising polyacrylamide, of nucleic acid fragments produced during an enzymatic DNA sequencing reaction present in a solution comprising at least 0.2% (w/v) of a reagent selected from the group consisting of glycerol, dithiothreitol, trehalose, and ethylene glycol comprising the steps of:

applying said solution to an electrophoretic gel, wherein said gel is a DNA sequencing gel comprising polyacrylamide and electrophoresing said fragments into said gel in the presence of a buffer lacking boric acid or borate or a derivative thereof which interacts with said reagent to form said complex.

2. The method of any of claim 1 wherein said buffer comprises an acid portion chosen from acetic acid, carbonic acid, glycine, serine, taurine, tricine, and bicine.

3. The method of any of claim 1 wherein said buffer lacks EDTA.

* * * * *